United States Patent
Aldridge et al.

(10) Patent No.: US 11,542,634 B2
(45) Date of Patent: Jan. 3, 2023

(54) PARTICLE-FILLED FIBER AND ARTICLES FORMED FROM THE SAME

(71) Applicant: Illinois Tool Works Inc., Glenview, IL (US)

(72) Inventors: Emily Aldridge, Glenview, IL (US); Robert Martin, Glenview, IL (US); Karen Mertins, Glenview, IL (US)

(73) Assignee: Illinois Tool Works Inc., Glenview, IL (US)

( * ) Notice: Subject to any disclaimer, the term of this patent is extended or adjusted under 35 U.S.C. 154(b) by 17 days.

(21) Appl. No.: 16/934,163

(22) Filed: Jul. 21, 2020

(65) Prior Publication Data

US 2020/0347519 A1   Nov. 5, 2020

Related U.S. Application Data

(63) Continuation-in-part of application No. 14/705,565, filed on May 6, 2015, now Pat. No. 10,753,022.
(Continued)

(51) Int. Cl.
*D01F 1/10* (2006.01)
*D01F 6/06* (2006.01)
(Continued)

(52) U.S. Cl.
CPC ............... *D01F 1/10* (2013.01); *C08K 3/08* (2013.01); *C08K 3/30* (2013.01); *C08L 23/12* (2013.01);
(Continued)

(58) Field of Classification Search
CPC .. D01D 5/08; D01F 1/10; D01F 1/106; D10B 2509/00–08; G01N 23/06
(Continued)

(56) References Cited

U.S. PATENT DOCUMENTS 3,068,547 A   12/1962   L'Hommedieu
3,491,802 A   1/1970   Mortensen et al.
(Continued)

FOREIGN PATENT DOCUMENTS

CN   101597811 A   12/2009
CN   101671864 A   3/2010
(Continued)

OTHER PUBLICATIONS

Gangolli, S. "Cobalt and Nickel." The Dictionary of Substances and Their Effects, The Royal Society of Chemistry, Cambridge, 1999, pp. C369 and N44. (Year: 1999).*
(Continued)

*Primary Examiner* — Larissa Rowe Emrich
(74) *Attorney, Agent, or Firm* — Blue Filament Law PLLC

(57) ABSTRACT

A non-woven fiber article for use in a food, medical, or pharmaceutical production environment including a melt-spun polymer fiber is provided having a cross-section and a length and a detectable particulate present in an amount of 20 to 80 weight percent loadings of metal or 10 to 80 weight percent loadings of radiopaque particles to render the polymer fiber detectable by magnetic or X-ray detection, alone or in combination with a secondary functional particulate distributed with the polymer fiber to render the polymer fiber chemically responsive to a chemical reactant, change in pH or temperature. The detectable particulate and the secondary functional particulate are each independently present in a core, a sheath, or both portions of polymer matrix. A process of detecting a fabric made from such a fiber. The fabric article passes through detector. A signal is collected from the detector indicative of the presence of the fabric article.

17 Claims, 5 Drawing Sheets

Related U.S. Application Data

(60) Provisional application No. 62/029,063, filed on Jul. 25, 2014.

(51) Int. Cl.

| | |
|---|---|
| *D04H 1/4234* | (2012.01) |
| *D04H 1/4382* | (2012.01) |
| *G01N 23/083* | (2018.01) |
| *G01N 33/36* | (2006.01) |
| *C08L 23/12* | (2006.01) |
| *C08K 3/08* | (2006.01) |
| *C08K 3/30* | (2006.01) |
| *B82Y 5/00* | (2011.01) |
| *B82Y 40/00* | (2011.01) |
| *B82Y 30/00* | (2011.01) |

(52) U.S. Cl.
CPC ............ *D01F 6/06* (2013.01); *D04H 1/4234* (2013.01); *D04H 1/4382* (2013.01); *G01N 23/083* (2013.01); *G01N 33/367* (2013.01); *B82Y 5/00* (2013.01); *B82Y 30/00* (2013.01); *B82Y 40/00* (2013.01); *C08K 2003/0831* (2013.01); *C08K 2003/3045* (2013.01); *C08K 2201/011* (2013.01); *C08L 2203/12* (2013.01)

(58) Field of Classification Search
USPC .................... 428/372, 392–395, 400, 402
See application file for complete search history.

(56) References Cited

U.S. PATENT DOCUMENTS

| | | | |
|---|---|---|---|
| 3,620,875 A | 11/1971 | Guglielmo, Sr. et al. | |
| 3,633,533 A | 1/1972 | Allen et al. | |
| 3,701,165 A | 10/1972 | Huddleston | |
| 3,756,241 A | 9/1973 | Patience | |
| 3,756,512 A | 9/1973 | Dyal | |
| 3,867,935 A | 2/1975 | Eisdorfer et al. | |
| 3,911,922 A * | 10/1975 | Kliger ...................... A61F 13/44 |
| | | | 604/362 |
| 3,929,659 A | 12/1975 | Graham | |
| 4,068,666 A | 1/1978 | Shiff | |
| 4,155,487 A | 5/1979 | Blake | |
| 4,185,626 A | 1/1980 | Jones et al. | |
| 4,207,376 A * | 6/1980 | Nagayasu ................ D01D 5/34 |
| | | | 264/172.12 |
| 4,345,718 A | 8/1982 | Horvath | |
| 4,620,646 A | 11/1986 | Crapser | |
| 4,620,656 A | 11/1986 | McClay et al. | |
| 4,645,499 A | 2/1987 | Rupinskas | |
| 4,664,971 A | 5/1987 | Soens | |
| 4,692,380 A | 9/1987 | Reid | |
| 4,718,897 A | 1/1988 | Elves | |
| 4,935,019 A | 6/1990 | Papp, Jr. | |
| 4,938,901 A | 7/1990 | Groitzsch et al. | |
| 5,045,080 A | 9/1991 | Dyer et al. | |
| 5,112,325 A | 5/1992 | Zachry | |
| 5,178,354 A | 1/1993 | Engvall | |
| 5,183,614 A | 2/1993 | Champion | |
| 5,204,162 A * | 4/1993 | Ketcham ..................... B01J 2/18 |
| | | | 419/23 |
| 5,337,912 A | 8/1994 | Jochem | |
| 5,379,924 A | 1/1995 | Taylor | |
| 5,425,996 A | 6/1995 | Wilkie et al. | |
| 5,522,921 A | 6/1996 | Custer | |
| 5,670,239 A | 9/1997 | Hampp | |
| 5,793,214 A | 8/1998 | Wakamatsu | |
| 5,888,640 A | 3/1999 | Marotta et al. | |
| 5,897,673 A | 4/1999 | Nishida et al. | |
| 5,931,824 A | 8/1999 | Stewart et al. | |
| 5,952,099 A | 9/1999 | Asher et al. | |
| 6,177,113 B1 | 1/2001 | Kress et al. | |
| 6,200,628 B1 | 3/2001 | Rozumek et al. | |
| 6,332,993 B1 | 12/2001 | Jen | |
| 6,356,782 B1 | 3/2002 | Sirimanne et al. | |
| 6,371,904 B1 | 4/2002 | Sirimanne et al. | |
| 6,395,147 B1 | 5/2002 | Wheat et al. | |
| 6,502,726 B1 | 1/2003 | Yquel | |
| D487,353 S | 3/2004 | Wolf | |
| 6,825,249 B1 | 11/2004 | Takeda et al. | |
| 6,896,759 B2 | 5/2005 | Fujisawa et al. | |
| 7,015,156 B2 | 3/2006 | Maldonado et al. | |
| 7,038,766 B2 | 5/2006 | Kerns et al. | |
| 7,044,957 B2 | 5/2006 | Foerster et al. | |
| 7,053,013 B1 | 5/2006 | Nosov et al. | |
| 7,222,727 B2 | 5/2007 | Aisenbrey | |
| 7,229,417 B2 | 6/2007 | Foerster et al. | |
| 7,242,176 B2 | 7/2007 | Thomason | |
| 7,465,847 B2 | 12/2008 | Fabian | |
| 7,568,590 B1 | 8/2009 | Gross et al. | |
| 7,625,397 B2 | 12/2009 | Foerster et al. | |
| 7,631,767 B2 | 12/2009 | May et al. | |
| 7,668,582 B2 | 2/2010 | Sirimanne et al. | |
| 7,703,674 B2 | 4/2010 | Stewart et al. | |
| 7,795,491 B2 | 9/2010 | Stewart et al. | |
| 7,952,375 B2 | 5/2011 | Eldridge et al. | |
| 8,075,985 B2 | 12/2011 | Lee et al. | |
| 8,093,161 B2 | 1/2012 | Bansal et al. | |
| 8,267,681 B2 | 9/2012 | Gupta et al. | |
| 8,410,006 B2 | 4/2013 | Chappas et al. | |
| 8,980,982 B2 | 3/2015 | Martin et al. | |
| 9,303,342 B2 | 4/2016 | Wang et al. | |
| 2004/0031798 A1 | 2/2004 | Fox et al. | |
| 2004/0142495 A1 | 7/2004 | Hartman et al. | |
| 2004/0154072 A1 | 8/2004 | Connor | |
| 2005/0153857 A1 | 7/2005 | Sherry et al. | |
| 2005/0236407 A1 | 10/2005 | Aisenbrey | |
| 2007/0003761 A1 * | 1/2007 | Miyazono ............ D03D 15/507 |
| | | | 428/375 |
| 2007/0205529 A1 | 9/2007 | May et al. | |
| 2007/0219516 A1 | 9/2007 | Patel et al. | |
| 2008/0290649 A1 | 11/2008 | Klein et al. | |
| 2009/0302241 A1 | 12/2009 | Abe et al. | |
| 2010/0087731 A1 | 4/2010 | Ramachandran | |
| 2010/0124644 A1 | 5/2010 | Hein et al. | |
| 2010/0187171 A1 | 7/2010 | Gupta | |
| 2010/0187712 A1 | 7/2010 | Gupta et al. | |
| 2010/0221969 A1 * | 9/2010 | Chen ........................ D01F 1/10 |
| | | | 442/189 |
| 2011/0207237 A1 * | 8/2011 | Sai .................. G01N 33/54373 |
| | | | 436/518 |
| 2011/0231983 A1 | 9/2011 | Chan | |
| 2011/0277261 A1 | 11/2011 | Hasket et al. | |
| 2012/0000691 A1 | 1/2012 | Shah et al. | |
| 2012/0164907 A1 | 6/2012 | Restuccia et al. | |
| 2012/0289107 A1 * | 11/2012 | Beissinger ............ D04H 1/4258 |
| | | | 442/1 |
| 2015/0132574 A1 | 5/2015 | Aldridge et al. | |
| 2015/0183090 A1 | 7/2015 | Hsu et al. | |
| 2016/0024699 A1 | 1/2016 | Aldridge et al. | |

FOREIGN PATENT DOCUMENTS

| | | |
|---|---|---|
| EP | 0160560 A2 | 11/1985 |
| EP | 0942804 A1 | 9/1999 |
| EP | 1217105 A1 | 6/2002 |
| EP | 1650556 A1 | 4/2006 |
| EP | 1776006 A1 | 4/2007 |
| GB | 2315698 A | 2/1998 |
| GB | 2372934 A | 9/2002 |
| JP | H0931749 A | 2/1997 |
| JP | 2002020554 A | 1/2002 |
| JP | 2005009024 A | 1/2005 |
| JP | 2008303525 A | 12/2008 |
| JP | 2014095170 A | 5/2014 |
| KR | 890001835 B1 | 5/1989 |
| KR | 20010086868 A | 9/2001 |
| KR | 20020050902 A | 6/2002 |
| WO | 9305101 A1 | 3/1993 |
| WO | 0023275 A1 | 4/2000 |
| WO | 2004094763 A2 | 11/2004 |

(56) References Cited

FOREIGN PATENT DOCUMENTS

| WO | 2005061649 A1 | 7/2005 |
|----|---------------|--------|
| WO | 2006026823 A1 | 3/2006 |
| WO | 2007012898 A1 | 2/2007 |
| WO | 2008146529 A1 | 12/2008 |
| WO | 2017048897 A1 | 3/2017 |

OTHER PUBLICATIONS

International Search Report dated Jun. 27, 2012 for International Application No. PCT/US2012/030249 filed Mar. 23, 2012.
European Search Report dated Jan. 27, 2017 for European Application No. 16188423 filed Mar. 23, 2012.
Dong, W. et al., "Novel fabrication of magnetic thermoplastic nanofibers via melt extrusion of immiscible blends", Polymers Advanced Technologies, 2012, 5 pages, © 2012 John Wiley & Sons, Ltd.; DOI: 10.1002/pat.3051.
Niu, S. et al., "Fabrication of magnetic nanofibers via surface-initiated RAFT polymerization and coaxial electrospinning", Reactive & Functional Polymers, 2013 (Published online: Aug. 3, 2013), pp. 1447-1454, vol. 73, © 2013 Elsevier Ltd.; DOI: 10.1016/j.reactfunctpolym.2013.07.011.
International Search Report dated Jan. 9, 2015 for International Application No. PCT/US2014/061466 filed Oct. 21, 2014.
Written Opinion of the International Searching Authority dated Oct. 2, 2015 for International Application No. PCT/US2015/041461 filed Jul. 22, 2015.
International Search Report dated Nov. 28, 2016 for International Application No. PCT/US2016/051836 filed Sep. 15, 2016.
International Search Report dated May 17, 2019 for International Application No. PCT/US2019/018013 filed Feb. 14, 2019.

\* cited by examiner

PARTICLE-FILLED FIBER AND ARTICLES FORMED FROM THE SAME

CROSS-REFERENCE TO RELATED APPLICATIONS

This application is a non-provisional application that claims priority benefit of Int'l Patent Appln. No. PCT/US2015/041461, filed Jul. 22, 2015 and U.S. patent application Ser. No. 14/705,565, filed on May 6, 2015, which in turn claims priority benefit of U.S. Provisional Patent Appln. No. 62/029,063, filed Jul. 25, 2014, the contents of which are hereby incorporated by reference.

FIELD OF THE INVENTION

The present invention relates to the technical field of polymeric composite fibers, and in particular to polymeric fibers with high loadings of functional particulate that impart specific physical, mechanical or chemical properties to the articles formed from such fibers.

BACKGROUND OF THE INVENTION

Many industries have a need for functional polymers and articles made therefrom. By way of example, a food, medical, or pharmaceutical production line maintains tight audit control of service articles that enter the medical or manufacturing facility to assure such articles do not accidently enter the process or production stream as a contaminant that can be fragmented into dangerous shards. Historically, plastics have been precluded from some environments due the inability to locate such articles with product screening metal or X-ray detectors. Recently, plastic articles have been developed that are filled with metal particulate or barium sulfate, as detailed US Patent Application Publication US20120241589 that are detectable with magnetic or X-ray detectors, yet still process as injection moldable thermoplastics and operate in manner similar to their unfilled conventional counterparts.

By way of example, U.S. Pat. No. 5,897,673 teaches fibers containing fine metallic particles that are cross-linked to the polymeric fiber. While various pure metals are contemplated in the literature, little attention has been paid to the unique problems associated with stainless steel particulate or other functional particulates. As many manufactured substances can only be exposed to stainless steel or other functional particulates, the lack of stainless steel or other functional particle filled fibers precludes the usage of many useful articles from these controlled manufacturing sites. By way of example various wipes, hair covers, suits, aprons and shoe covers and other manufacturing aids or personal protective equipment if made from stainless steel or other functional particulates containing fibers could allow better quality control of manufacturing with less stringent audit processes, as any such articles lost in a production stream could be detected by X-ray or magnetic anomaly. However, injection molded parts containing loading of metals or electron dense substances needed for detection are limiting in terms of the materials that can be formed.

Thus, there exists a need for a spun thermoplastic fiber filled with particulate, the particulate rendering a resultant non-woven article either detectable in a production context alone or also to include additional functional particulate. There also exists a need for such fibers that process and retain properties of conventional thermoplastic fibers to promote production of various articles from fibers that have the added benefit of imparting functional properties while operating in a manner similar to conventional articles.

SUMMARY OF THE INVENTION

A melt-spun polymer fiber is provided having a cross-section and a length. A detectable particulate present in an amount of 20 to 80 total weight percent metal particulate to render the polymer fiber detectable by magnetic detection or 10 to 80 total weight percent radiopaque particulate to render the polymer fiber detectable by X-ray detection, alone or in combination with a secondary functional particulate distributed in or on the polymer fiber to render the polymer fiber chemically responsive to a chemical reactant, change in pH or temperature. The detectable particulate and the secondary functional particulate are each independently present in a core, a sheath, or both portions of polymer matrix. A process of detecting a fabric made from such a fiber is provided. The fabric article passes through detector. A signal is collected from the detector indicative of the presence of the fabric article.

A particle filled spun fiber that when formed into a nonwoven material affords an article that is detectable so as to prevent retention in a medical or production context. The resultant article is also rendered functional through the inclusion of additional types of particulate. Non-woven fabrics are formed that have additional functionality in the context of filtration; blood clotting; detection of changes in pH, temperature, of the presence of a chemical or biologic; or can be solidified to form a form fitting mass. In a prototypical form sheets in particle filled non-woven fibers are formed as wipes for various wiping applications such as personal hygiene, medical procedures, or equipment or parts cleaning. The present invention may also be used to manufacture various personal protective articles from such sheets such as shoe covers, hair nets, beard nets, sleeve covers, aprons or any other protective article that can be used in the food, medical, pharmaceutical, or other industries where there is a concern regarding the need for specific physical, chemical, or mechanical properties. The material may also be used to manufacture other materials illustratively including filters and filter media and electrostatically dissipative products.

A detectable particulate-containing article afford the benefit of subsequent detection and inventory control to an otherwise conventional article, and with the addition of functional particulate material included in the fiber affords functionality unique to various fields of endeavor. Detectable particulate additives are present from 2.0 to 50.0 weight percent loadings of metal or 10 to 80 weight percent loadings of radiopaque particles in the melt-spun fiber, for manufacturing the filled-fiber non-woven material. This is accomplished by incorporating detectable particles with a size of D90<31 micron or smaller into a monofilament, composite or bi-, tri-, or multi-component fiber in the spinning process. A secondary, functional particulate is added during or after the spinning process to impart additional functionality to the resulting non-woven article. One feature of the functional fibers is that a constituent of the composite or multi-component fiber is a removable sheath that upon removal exposes the underlying particles. The novel feature is that processing, cleaning, protective, or other non-woven articles formed with fibers containing the above referenced detectable particulate alone, or in combination with functional additives are used to impart detectability, as well as specific functional properties associated with the inclusion of secondary, functional particulate.

A fiber is provided with a polymer having a cross-section and a length. A particulate is distributed in the polymer in an amount to make the fiber detectable alone, or also functional. The particulate is present in a core, a sheath, or both portions of the fiber defined by a polymer matrix.

A process of detecting a fabric article is provided that includes the formation of a fiber in the form of a polymer having a cross-section and a length. A particulate is distributed in the polymer. A fiber is formed into a non-woven fabric. A fabric article may then be manufactured from the fabric. The fabric article provides an end-use functionality. A signal is collected from the X-ray detector or the magnetic detector indicative of the presence of the fabric article.

BRIEF DESCRIPTION OF THE DRAWINGS

The present invention is further detailed with respect to the following figures that depict various aspects of the present invention.

FIGS. 2A-2H are fiber photographs and their corresponding X-ray films: Photograph of extruded polypropylene fiber containing 30.0 wt % barium sulfate particles (FIG. 2A), X-ray film of extruded polypropylene fiber containing 30.0 wt % barium sulfate particles (FIG. 2B), photograph of pad cut from meltblown polypropylene fiber containing 30.0 wt % barium sulfate particles (FIG. 2C), X-ray film of pad cut from meltblown polypropylene fiber containing 30.0 wt % barium sulfate particles (FIG. 2D), X-ray transmission images of barium sulfate/propylene meltblown pads clockwise from the first quadrant for 3, 6, 20, and 10 layers that are produced with higher die temperature to yield a comparatively denser pad, as compared to those of FIG. 2F (FIG. 2E), X-ray transmission images of barium sulfate/propylene meltblown pads clockwise from the first quadrant for 3, 6, 20, and 10 layers that are produced with lower die temperature to yield a fluffier pad (FIG. 2F), X-ray transmission image of barium sulfate/propylene meltblown as a 10 layer pad submerged in 3.5 inches of water to simulate tissue with a US quarter used as a weight to keep the pad submerged (FIG. 2G), and X-ray transmission image of barium sulfate/propylene meltblown as a 20 layer pad submerged in 3.5 inches of water to simulate tissue with two US quarters used as a weight to keep the pad submerged (FIG. 2H).

DETAILED DESCRIPTION OF THE INVENTION

Figure 1A:
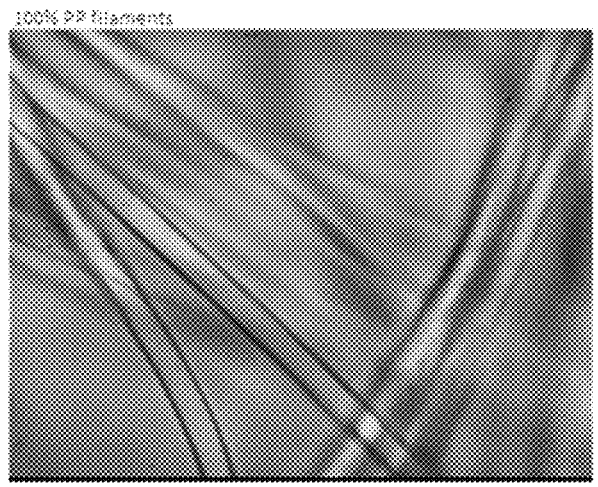
FIGS. 1A-1C and FIGS. 2A-2F Conventional prior art 100% polypropylene (PP) fibers (upper left FIG. 1A), Optical micrograph of meltblown polypropylene fiber containing 30.0 wt % barium sulfate particles at 500× magnification (FIG. 1B), UV micrographs of extruded (meltspun without drawing) polypropylene fiber containing 30.0 wt % barium sulfate particles at 200× magnification (FIG. 1C).

The present invention has utility as non-woven article formed from a fiber that is electromagnetic spectrally detectable that may also have functional properties that are suitable for usage in a variety of fields and production environments illustratively including food production, medical, and pharmaceutical production environments. Through inclusion of a secondary functional particulate, an additional functionality is imparted to the resulting article. Such functionality includes drug delivery; filtration; blood clotting; detection of changes in pH, temperature, of the presence of a chemical or biologic; or can be solidified to form a form fitting mass. In one aspect of the present invention it is possible to spin both PP and PET metal detectable fibers in the range of at least 2.0 denier per filament. This is accentuated by the fact that the inclusion of dense metal particles into the fiber "skews" the denier count. Since denier is a weight per unit length measurement, it is possible to obtain fibers that are smaller in diameter than the same denier pure polymer fibers.

As used herein, the term "fiber" defines both fibers of finite length, illustratively including conventional preselected length fiber, as well as substantially continuous structures, such as continuous filaments, unless otherwise indicated. The fibers of the present invention are appreciated to be hollow or solid fibers, and further can have a substantially round or circular cross-section or cross-sections of different symmetry space groups with other cross-sections illustratively including oval; circular; multi-lobal; lobular; and polygonal such as triangular, square, rectangular, trapezoidal, pentagonal, and hexagonal. An article of the present invention in some embodiments has a sheath that varies in polymer or particulate, with the variation being as to composition or concentration, or both such properties.

As used herein, the term "multi-component fibers" is defined to include preselected length fiber and continuous filaments with two or more discrete structured domains of deliberately different composition or component concentration and is intended to specifically include sheath/core and island configurations.

As used herein, the term "yarn" defines multiple fibers wound together into a single continuous strand.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

It is appreciated that both the cross-sectional shape of the fiber and the configuration of the particulate and other components therein depends upon the equipment that is used in the preparation of the fiber, the process conditions, and the melt viscosities of the various components. A wide variety of fiber configurations are readily produced according to the present invention to achieve loadings sufficient for metal or X-ray detection. Generally, as illustrated in the figures, a fiber according to the present invention is a single or multi-component composite fiber formed from a melt of one or more polymeric materials loaded with one or more metallic or radiopaque materials as specified below.

The polymeric component of an inventive fiber is readily selected from any of the types of polymers known in the art that are capable of being formed into fibers, including polyolefins, polyvinyl, polyvinyl alcohol, polyesters, polyamides, co-polymers containing any of the aforementioned polymers as blocks of a copolymer, and combinations thereof. Specific polyolefins operative herein illustratively include polypropylene; polyethylene; polybutene; and polyisobutylene; polyamides such as NYLON 6 and NYLON 6,6; polyacrylates; polystyrenes; polyurethanes; acetal resins; polyethylene vinyl alcohol; polyesters illustratively including polyethylene terephthalate (PET), polyethylene naphthalate, polytrimethylene terephthalate, poly(1,4-cyclohexylene dimethylene terephthalate) (PCT), polycarbonates; and aliphatic polyesters illustratively including polylactic acid (PLA); polyphenylene sulfide; thermoplastic elastomers; polyacrylonitrile; cellulose and cellulose derivatives; polyaramids; acetals; fluoropolymers; copolymers and terpolymers thereof, and mixtures or blends thereof, and without regard as whether a given polyolefin is syndiotacic, eutectic, isotactic, or atactic.

Specific examples of aliphatic polyesters operative in the present invention include fiber forming polymers formed from a combination of an aliphatic glycol such as ethylene glycol, propylene glycol, butylene glycol, hexanediol, octanediol or decanediol or an oligomer of ethylene glycol (e.g., diethylene glycol or triethylene glycol) with an aliphatic dicarboxylic acid such as succinic acid, adipic acid, hexanedicarboxylic acid or decaneolicarboxylic acid; or the self-condensation of hydroxy carboxylic acids other than poly(lactic acid), such as polyhydroxy butyrate, polyethylene adipate, polybutylene adipate, polyhexane adipate, and copolymers containing the same. Aromatic polyesters operative in the present invention include fiber forming polymers formed from polyesters of alkylene glycols having 2-10 carbon atoms and aromatic diacids; polyalkylene naphthalates, which are polyesters of 2,6-naphthalenedicarboxylic acid and alkylene glycols, as for example polyethylene naphthalate; or polyesters derived from 1,4-cyclohexanedimethanol and terephthalic acid, as for example polycyclohexane terephthalate. Exemplary polyalkylene terephthalates include polyethylene terephthalate (also PET) and polybutylene terephthalate.

The identity of electromagnetic spectrally detectable particulate operative herein are largely dictated by compatibility with the resin and susceptibility to detection by the organic production stream detection equipment so employed. Electromagnetic spectrally detectable particulate operative herein illustratively include stainless steel, ferrous metals, zinc, aluminum, alloys containing such metals of aluminum, zinc and iron. Barium sulfate and iodine containing compounds represent inorganic, non-metallic, electromagnetic spectrally detectable particulate operative herein with a high degree of radio opacity. Typical loadings of such inventive additives commonly range from 1 to 80 total weight percent of the injection moldable resin. Preferably, the additive is selected to be food grade or inert relative to the pharmaceutical or other production stream.

In some inventive embodiments that are complaint with food, medical and pharmaceutical processing standards, the particulate is stainless steel. Other compositions of particulate to render an inventive fiber magnetic or X-ray signal detectable include iron, bronze (a copper-based alloy that typically consists of approximately 88% copper and 12% tin. Trace amounts of other metals, such as aluminum, manganese, phosphorus, and silicon, may also be present in the alloy), brass (a metal alloy that primarily consists of copper and zinc and other metals such as lead, tin, iron, aluminum, silicon, and manganese to produce unique combinations of characteristics), steel, barium salts, cobalt, titanium, tin, copper, tungsten, platinum, silver, bismuth, zinc, lead, molybdenum, neodymium-iron, samarium-cobalt, alloys of any of the aforementioned, oxides of any of the aforementioned metals, nitrides of any of the aforementioned.

It is appreciated that alloys of any of the aforementioned include any of the above listed metals combined with any other known metal including those listed such as iron, bronze, brass, steel, barium salts, cobalt, titanium, tin, copper, tungsten, platinum, silver, bismuth, zinc, lead, molybdenum, neodymium-iron, and samarium-cobalt, as well as other light weight metals such as aluminum, magnesium, and boron. Such alloys provide desirable properties such as low weight (e.g. aluminum), higher conductivity (e.g. copper), or resistance to corrosion. By way of non-exhaustive example, alloys of any of the aforementioned include aluminum iron alloy, which according to embodiments has a chemical composition of Al-46% Fe-25%; aluminum bronze alloys including C95200, C95400, C95500, C95800, C95900, which contain approximately 9-14% aluminum and 4% iron while Nickel Aluminum Bronze contains approximately 9-11% aluminum, 4% iron and 5% nickel and Common; aluminum-steel alloy, which is more flexible, lightweight and stronger than any kind of steel ever made and is 13 percent less dense compared to normal steel, and with a comparable strength-to-weight ratio compared to titanium alloys; Cobalt Aluminum Alloy, which includes at least 10% aluminum; titanium Grade 5, which is classified as an alpha-beta alloy, and consists of 6% aluminum, 4% vanadium, and trace amounts of iron; Low-tin aluminum-base alloys (5 to 7% Sn) containing small amounts of strengthening elements, such as copper and nickel; alloys containing 20 to 40% tin and remainder aluminum, which show excellent resistance to corrosion; Aluminum copper alloy, which according to embodiments has a chemical make-up of Al-46% Cu-54%; a platinum aluminum alloy such as $PtAl3$; aluminum silver alloy, which has a chemical composition of 89-91% aluminum and 9-11% silver; 10% Bismuth Aluminum Alloy; Zinc-aluminum alloy, such as ZA-27, which consists of 27 percent aluminum and 2.2 percent copper; 8% Lead Aluminum Alloy; and Aluminum Molybdenum such as AL1633.

It is appreciated that cobalt alloys such as cobalt-samarium, and neodymium alloys have exceptionally high magnetic moments that allow for magnetic detection at lower weight loading compared for ferrite. In some inventive embodiments, the stainless steel is ferromagnetic and detectable by magnetic induction coil detectors. Specific grades of stainless particulate operative herein include 300 series, 400 series and in particular 306 (L), 316, 405, and 430 compositions. By way of non-exhaustive example, Type 405 stainless steel has a chemical composition that includes iron, chromium, manganese, silicon, aluminum, carbon, phosphorus, and sulfur, which imparts properties such as preventing hardening when cooled from high temperatures. It is appreciated that in addition to spherical particulate shown in FIGS. 1B-1D; prolate spheroids, oblate spheroids, and cylindrical rods of the particulate are used in the present invention. It has been surprisingly discovered that non-spherical particulate tends to align along a fiber length with the shortest linear dimension axis from the three orthogonal axes of X-Y-Z oriented generally perpendicular to the longest axis length of the fiber.

According to embodiments, a radiopaque particulate, that is particulate having high degree of radio opacity, is included in the polymer material. Radiopaque refers to any substance having the property of absorbing X-rays and of thus influencing the radiological image obtained. While Barium and Iodine are the two main radiopaque substances used in radiology, other materials are also contemplated by the term radiopaque, such as stainless steel, iron, bronze, brass, steel, barium salts, cobalt, titanium, tin, copper, tungsten, platinum, silver, bismuth, zinc, lead, molybdenum, neodymium-iron, and samarium-cobalt, as well as other light weight metals such as aluminum, magnesium, and boron.

The present invention attempts to retain the processing and performance properties of the native polymer while imparting the ability to render the fiber and articles formed therefrom X-ray or magnetic anomaly detectable. This is achieved by inclusion of particulate having a shortest linear dimension, as measured from among the three orthogonal Cartesian coordinate axes X-Y-Z that is less than or equal to one half the fiber cross-sectional average dimension along the three orthogonal Cartesian coordinate axes X-Y-Z. For the purposes of calculation of the particulate dimension, the average particle dimension is used for polydisperse particulate. The detectable particulate with a size of D90<31 micron or smaller. By way of example, a circular cross-section fiber with a diameter of 35 microns is loaded with spherical particulate having a diameter of less or equal to 17 microns. In some inventive embodiments containing cylindrical rod particulate, the ratio of rod length to diameter is between 1.3-20:1 and in still other embodiments between 1.5-8:1. According to embodiments, the shape of the particulate is deformed due to the extrusion of the polymer fiber. That is, after mixing of the particulate with polymer material, the mixed particulate and polymer material are extruded through small openings to form the inventive fibers. During this extrusion process some of the particulate contained in the polymer material collides with the extrusion die that forms the small openings. Given the speed at which the extrusion process takes place, the collision of the particulate with the extrusion die deforms at least some of the detectable particulate. Accordingly, some of the particulate may be spherical in shape while a plurality of the particulate is asymmetrically deformed or flattened and misshaped spherical particles formed from originally spherical particles.

According to embodiments, the particulate has an average x-y-z linear dimension such that at least 50% of the particles present in the plastic resin have an x-y-z average linear dimension of less than 100 microns. As used herein, "x-y-z average linear dimension" defines the average linear extent of a particle in three orthogonal directions defined by x axis, y axis, and z axis. More preferably, greater than 70% of the particles have an average x-y-z linear extent of less than 80 microns. Still more preferably, 90% of the additive particles have an average x-y-z linear extent of less than 50 microns. The additive is optionally pre-coated with one of the aforementioned resins to facilitate dispersion.

In certain embodiments, each of the polymeric components of an inventive fiber includes other substances known conventionally to modify a processing property or performance property. Such additive substances illustratively include antioxidants, stabilizers, surfactants, waxes, flow promoters, solid solvents, dyes, pigments, plasticizers, and combinations thereof. It is appreciated that a pigment can encompass a composition of a particulate material detailed above to impart detectability to the inventive fiber, and in such instances the pigment is compositionally distinct from the particulate and present in a lower weight percentage than the particulate.

It is appreciated that the loading of particulate to achieve X-ray or magnetic detection of articles formed from inventive fibers is dictated by factors including the X-ray cross-section or the magnetic susceptibility of a given particulate. Generally, ferromagnetic materials are detectable at loadings of from >2 total weight percent by magnetic induction detection. In those embodiments when the ferromagnetic material is a rare earth magnet, typical loadings are from 2 to 4 total weight percent for magnetic induction detection. In specific embodiments, where the particulate is magnetic stainless steel or any other electromagnetic spectrally detectable particulate, typical loadings are from 2 to 50 total weight percent. It is appreciated that the above typical loading can be exceeded, yet often at the expense of detrimentally influencing the ability to process or increasing material financial costs with only incremental improvements in detection. According to embodiments, where the particulate is a non-ferrous metal such as aluminum, copper, lead, nickel, tin, titanium, zinc, brass typical loadings are from 10 to 80 total weight percent, which particularly with light-weight metals such as aluminum allow for increased particulate loading within the polymer material to increase magnetic or x-ray detection without significantly increasing the weight of the inventive fiber.

Specific embodiments of the invention incorporate secondary functional additives into the manufacture of nonwoven materials, which allow for the particulate-containing article to be used in a manner making benefit of the functional particulate material included in the fiber. Embodiments of the invention incorporate functional additive particulate at 0.01 to 5.0 weight percent loadings in the melt-spun fiber, for the manufacturing the filled-fiber material to be used in various functional applications. One feature of the functional fibers is that a constituent of the composite or multi-component fiber is removable to expose the particles thereby imparting specific functionality. The novel feature is that processing, cleaning, and protective articles formed with fibers containing the above referenced functional additives may be used to impart specific functional properties.

Non limiting examples of uses for the functional particles may include the delivery of blood clotting chemicals or other topical medicines, and color changing particles for indicating changes in pH and temperature, as well as detection and identification of specific chemicals, virus, and bacteria. Temperature change is readily detected with plasmonic nanoparticles able to change perceived color including metal nanoparticles, alone or in combination with oxide shells that illustratively include gold, silver, and nickel. Oxide coatings operative herein illustratively include silica and iron oxide. It is appreciated that some of these secondary functional particles have a small signal in electromagnetic spectrally detectable instrumentation in comparison to the detectable particulate. pH change is readily detected qualitatively through incorporation of a pH indicator dye such as phenolphthalein impregnated into a paper or cellulosic particulate. Blood clotting particles include deformable microgel particles that are about 1 micron in diameter and similar to the size of platelets, the microgel particles being attached to human antibody fragments that recognize fibrin. Drug delivery is achieved with particles illustratively including poly-lactic-co-glycolic acid (PLGA), metal nanocrystals; silica or dendrimers. Particles having a size of between 2 nm and 5 microns are particularly well-suited for drug delivery.

Functional particles may also have reactive properties. Non limiting examples of reactive particles may be particles that undergo an endothermic or exothermic reaction upon exposure to air and illustratively include iron particles. It is appreciated that based on the temperature generated and the melt properties of the coupled fiber, can induce fusion between contiguous fibers. In other embodiments, the particles are reacted with reagents that induce covalent bonding between particles. By way of example metal particles are readily joined through disulfides; dicarboxylates; polycarboxylates such are acrylates; diamines; polyamines such as cyclen; or combinations thereof. As a result, an inventive particle filled fiber mass is solidified by exposure to such a reagent. The resultant solidified fiber mass is useful in a variety of applications including filtration, leak treatment, or blood clotting. Non-limiting examples of filtration applications illustratively include water purification, bacteria, viruses, detrimental water-borne chemicals, and separation of metal fines. Further non-limiting example applications of the inventive reactive particles may include solar energy generation, addition of abrasiveness or to deliver and apply a polish, and reactive particles that change colors or shape with induction of electricity.

Figures 1B, 1C:
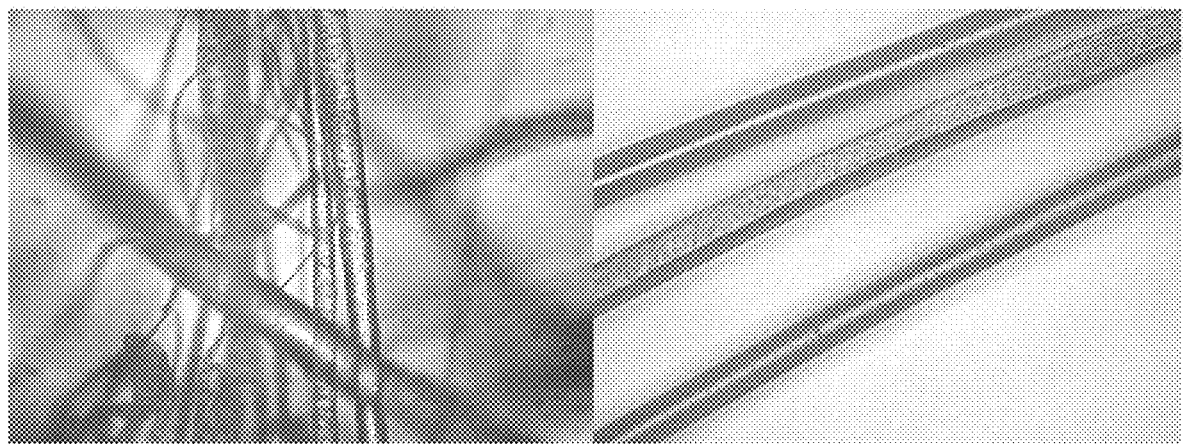

In order to manufacture fibers of the present invention, particles are compounded with one or more suitable pre-polymeric or polymeric compounds, as defined above that will form the basic fiber structure. The compounded material then undergoes a melt-spinning process and forms metal/polymer composite fibers. Without intending to be bound to a particular theory, the melt-spinning process tends to align asymmetric particles with the shortest linear dimension axis along the direction of fiber draw. In particular inventive embodiments, the particulate forms protrusions extending from the sides of the fibers, as seen in FIGS. 1B-1C. These protrusions have the added benefit of increase fiber surface area for a given length of fiber, and also appear to increase the energy needed to pull contiguous fibers from one another. With adjustment of melt temperature and draw rates, and in some instances modification of additive substances, inventive fibers are produced that have a homogenous distribution of particulate along the length of the fiber and retain 70% of the tensile strength of a given fiber composition absent particulate loading. In some embodiments a sheath is simultaneously drawn about a core. In still other embodiments, the sheath is free of particulate and the core is loaded with particulate. After extrusion, the fibers are drawn using technology known to those experienced in the art to their final tensile strength and diameter, preferably between 0.1 and 500 microns in diameter. In other embodiments, the fibers have a diameter or between 10 and 50 microns.

It has been surprisingly found that contrary to initial expectations, thermoplastic pellets loaded to up to 80 total weight percent of metals and up to 80 total weight percent of radiopaque particulate in spite of being more dense than non-particulate loaded thermoplastic pellets, are melt-spun without adjusting the feeding system, with the proviso that magnets conventional to the melt-spinning equipment are removed in those instances when the detected particulate is magnetic. Without intending to be bound to a particular theory, it is believed that the thermal retention of the particulate affects the filament cool down and draw behavior. Secondary functional particulate that is tolerant of the temperature and pressure conditions conventional to melt-spun fiber production are readily intermixed with the detectable particulate and incorporated into a fiber therewith into a fiber core, fiber sheath, or both.

While most polymers are more stable in the spinning process when only moderate draw force is applied, it has been surprisingly found that for a stock of particulate loaded pellets, applying higher draw force resulted in drip free spinning behavior.

Generally, for melt-spinning multi-component composite fibers, at least two polymers are extruded separately and fed into a polymer distribution system wherein the polymers are introduced into a spinneret plate. In the present invention, the particulate and at least one polymer are mixed or blended prior to extrusion using known techniques into extrudable pellets. In such inventive embodiments, the particulate is homogeneously dispersed throughout the polymer in which it is dispersed as the polymer streams are fed into the spinneret plate. It is appreciated that a particulate loaded pellets are used as a feedstock alone or intermixed with non-loaded pellets or pellets that vary in at least property of polymer composition, particulate size, particulate composition, additive composition, additive loading, particulate loading, or a combination of such properties. The polymers follow separate paths to the fiber spinneret and are combined in a spinneret hole. The spinneret is configured so that the extrudant has the desired overall fiber cross-section. In a prototypical, multi-component composite fiber according to the present invention, a core is extruded from particulate loaded pellets with a sheath formed from a particulate free pellet feedstock.

Following extrusion through the die, the resulting thin fluid strands, or filaments, remain in the molten state for some distance before they are solidified by cooling in a surrounding fluid medium, which may be, for example, chilled air blown through the strands. Secondary functional particulate is in some inventive embodiments applied to fibers as an aerosol in the chilled air carrier used to cool the spun fiber. Once solidified, the filaments are taken up on a godet roller or another take-up surface. Secondary functional particulate is in some inventive embodiments applied to fibers from a bath prior to, or after take up on godet roller or other surface. In a continuous filament process, the strands can be taken up on a godet which draws down the thin fluid streams in proportion to the speed of the take-up godet. In a spun-bond process, the strands can be collected in a jet, such as for example, an air attenuator, and blown onto a take-up surface such as a roller or a moving belt to form a spun-bonded web. In a melt-blown process, air is ejected at the surface of the spinneret which serves to simultaneously draw down and cool the thin fluid streams as they are deposited on a take-up surface in the path of cooling air, thereby forming a fiber web. Secondary functional particulate is in some inventive embodiments applied to spun-bonded web or a fiber web from an aerosol spray or a soaking bath.

Regardless of the type of melt spinning procedure used, generally the thin fluid streams are melt drawn down in a plastic state to orient the polymer molecules for good tenacity. Typical melt draw down ratios known in the industry are operative herein. In instances employing continuous filament or staple processes, in certain embodiments, the strands are drawn in the solid state with conventional drawing equipment, such as, for example, sequential godets operating at differential speeds.

Following drawing in the solid state, the continuous filaments in certain inventive embodiments are mechanically crimped and cut into a desirable fiber length, thereby producing staple fiber. The length of the staple fibers typically ranges from 25 to 50 millimeters, although the fibers may be cut to any desired length outside this range.

The multi-component fibers of the invention may be staple fibers, continuous filaments, or meltblown fibers. In general, staple fibers, multifilament, and spunbond fibers formed in accordance with the present invention may have a fineness of 0.1 to 500 microns per filament. In other embodiments, the filaments have a fineness diameter or between 10 and 50 microns per filament.

Meltblown filaments can have a fineness of 0.1 to 500 microns. Monofilament fibers may have a fineness of 0.1 to 500 microns. In other embodiments, the filaments have a fineness diameter or between 10 and 50 microns per filament.

The multi-component fibers of the invention are useful in the production of a wide variety of products, including without limitation nonwoven structures, such as but not limited to carded webs, wet laid webs, dry laid webs, spunbond webs, meltblown webs, and the like. The nonwoven webs can be bonded to transform the webs into a coherent nonwoven fabric using bonding techniques known in the industry. Exemplary bonding techniques for nonwoven webs include mechanical bonding, such as hydroentanglement and needle punching, adhesive bonding, thermal bonding, and the like. An example of thermal bonding is through air bonding, although other thermal bonding techniques, such as calendaring, microwave, or other RF treatments are readily employed.

An inventive fiber is well suited for use in a composite product, such as one with a dual surface in which a melt blown web includes a surface layer of fibers applied on the surface of the web to create a different textured surface relative to the web. By way of example, a polypropylene web with the detectable inventive particle filled fiber for the textured side. A composite example has a spun bond melt blown spun bond (SMS) where only one layer has the inventive detectable fibers. SMS is a very common composite nonwoven used in surgical gowns.

Articles formed according to the present invention from such particulate loaded fibers illustratively include non-limiting example of hair nets, protective suits, shoe covers, wipes, food packaging, aprons, beard covers, and mop heads. Such products in certain embodiments retain the operational properties of non-particulate loaded fibers of the same polymer composition, with the added attribute of being detectable with conventional food, medical and pharmaceutical production magnetic or X-ray detectors.

In some inventive embodiments, the inventive fibers are subjected to a coating, laminate, or otherwise cover the outer and/or inner surfaces of threads or layers of material contained within any final product without falling outside the scope of the invention. This is a practice well known to those experienced in the art, and is commonly used to impart non-stick, low-friction, or additional chemical and heat resistance properties to the final product. However, additional non-polymeric particles identical, similar, or fundamentally different to the particles already contained within the composite fibers of the invention, yet at the expense of lowering the overall metal content loading of the resultant article unless such treatments carry therewith particulate.

In certain embodiments of the present invention a fiber or core portion of a sheathed fiber has particulate protruding from the wall of the fiber and a concomitant relative depletion of particulate from the central region of a fiber. The inclusion of particulate protrusions and a centrally depleted fiber region has been found to afford considerable benefits in increasing the loading amount of particulate to detectable levels and the energy needed to slide fibers past one another.

In some embodiments of the present invention, following extrusion but prior to coating or lamination, the fibers or other non-woven creations of the invention are coated, dusted, or otherwise induced to carry on the exterior of individual filaments or layers additional particulate identical, similar, or fundamentally different to the particulate already contained within the composite fibers of the invention.

Particulate is most easily adhered to the outside of the fibers using a process which passes the extruded filament or non-woven creation through an enclosed chamber or fluidized bed, in which a fan system lifts and circulates the particulate throughout the air contained within the chamber such that a fraction of the particles that contact the filament will adhere to the surface.

In another embodiment of the invention, the fibers of the invention are used to make yarns. Yarns prepared for use in forming such woven and knit fabrics are similarly included within the scope of the present invention. Such yarns may be prepared from the continuous filament or spun yarns comprising staple fibers of the present invention by methods known in the industry, such as twisting or air entanglement.

An inventive non-woven fabric performs comparably to standard polymer containing fabrics with respect to most attributes, such as strength, durability, and hand, yet like the fibers exhibits properties which deviate significantly from those normally associated with the polymeric material by those experienced in the art, these unique properties beside detectability illustratively include high density, conductivity, electromagnetic shielding, cut-resistance, heat-resistance, and radiation shielding relative to the base polymer absent particulate loading.

The fibers or filament produced by this invention are suitable for application in knitting yarns. Further detail is outside the scope of this invention, but is well known to those experienced in the art. Once formed, the fabric may be cut, sewn, and otherwise tailored towards its final purpose using techniques also known to those skilled in the art. Furthermore, the fabric of the present invention may be manufactured, tailored, or otherwise altered or modified in design to exhibit other functional properties without falling outside the scope of the invention. These alterations or modifications illustratively include micro-perforations, patches of alternative fabrics, seamless knitting, fashion-centric alterations, dyeing or other coloring, and snaps, zippers, or other pockets for the addition and removal of personal effects, weights, or other articles to be carried or worn.

Additionally, the fabric of the present invention may be formed using a variety of different weaving or knitting techniques, both those known and unknown to those experienced in the art, without falling outside the scope of the present invention, which may result in additional qualities or properties of the final product. For example, processes and machinery have been developed to knit at very high speeds, at very low amounts of stress on the fiber or fabric, and in seamless and/or circular patterns and arrangements.

Additionally, the fabric of the present invention may be used to configure composite articles, both those known and unknown to those experienced in the art, without falling outside the scope of the present invention, which may result in additional qualities or properties of the final product. For example, processes and machinery have been developed to mechanically integrate microfiber thread loops into the detectable ground fabric to produce stitchbonded microfiber napped wipes.

Modern metal detection is based on creating a magnetic field with a transmitter coil and two receiving coils wired in reverse. The resulting field is interrupted when a conductive or magnetic contaminant passes through the field. The contaminant is detected by measuring the change in voltage above the change in voltage of non-contaminated product. If a contaminant is detected, that product is rejected. Contaminants are generally categorized as sphere equivalents in millimeters. The sensitivity and throughput of the contaminant detection process is machine dependent. According to embodiments, the detectable particulate includes a combination of a light weight such as aluminum metal and a heavy metal such as steel, such that detection equipment may be calibrated to detect such a combination specifically, thereby improving noise in the detection procedure.

X-ray inspection is based on density. The higher the density of the object being examined, the more energy is absorbed. X-ray detection measures how much energy is absorbed by a product or contaminant. X-ray detection can detect contaminants such as glass or bone that a metal detector will not detect. X-ray detection can perform other quality functions outside the scope of process or product contamination. The present invention focuses on contaminant and foreign object detection. The sensitivity and throughput of an X-ray inspection process is also machine dependent. As will be understood, electron dense materials such as stainless steel may be present in lower quantities in order to be X-ray detectable than less electron dense materials such as aluminum, which are x-ray detectable but at higher loadings than electron dense materials such as stainless steel.

The following are specific non-limiting examples of embodiments of the present invention. These examples should not be considered to be a limit on the scope of the appended claims.

Example 1

Spherical stainless steel particulate (430 series) having a Poisson size distribution and an average particle size of 12 microns is mixed into polypropylene (PP) to form pellets with a particulate loading of 12 percent. The particles are melt-spun by running through a five layer screen pack of mesh sized from 30 to 325. The melt is then drawn to a fiber as shown in FIGS. 1B-1C. Some of the particulate is noted to be flattened or misshaped.

Example 2

Figure 2A:
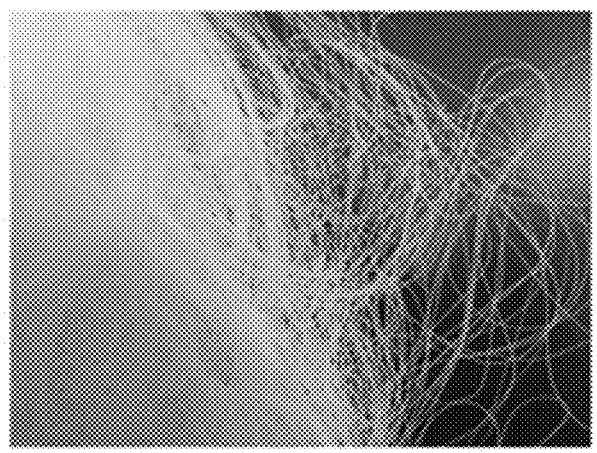
Figure 2B:
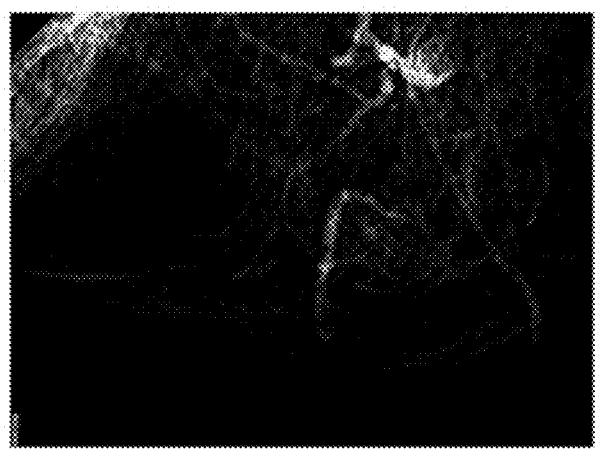
Figure 2C:
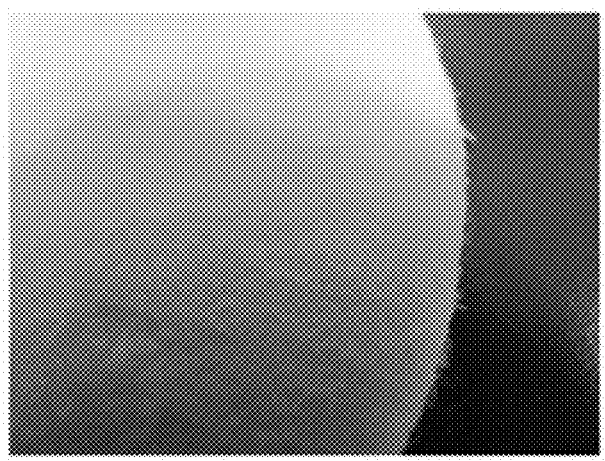
Figure 2D:
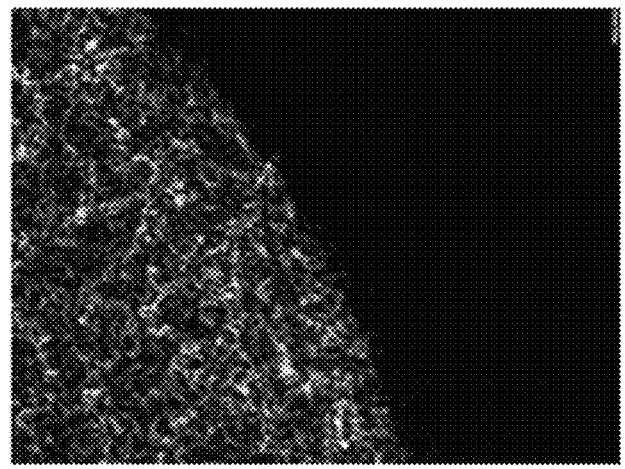
Figure 2E:
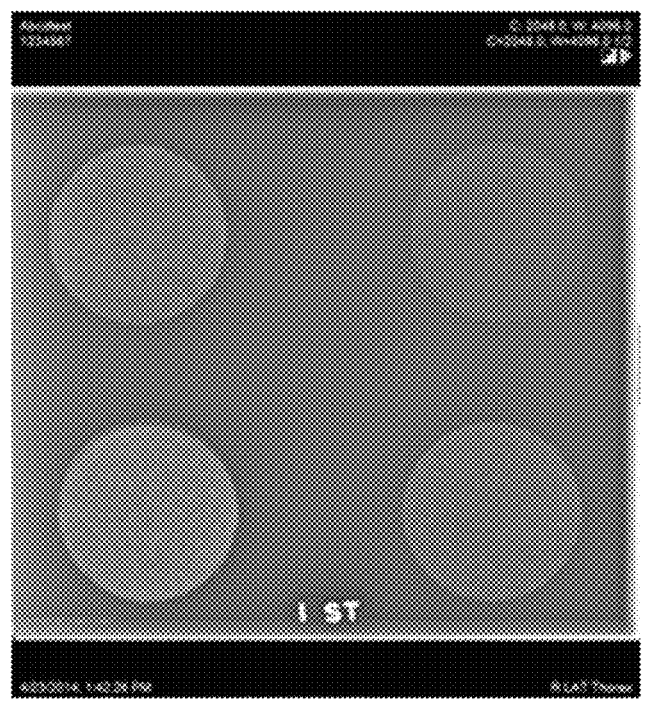
Figure 2F:
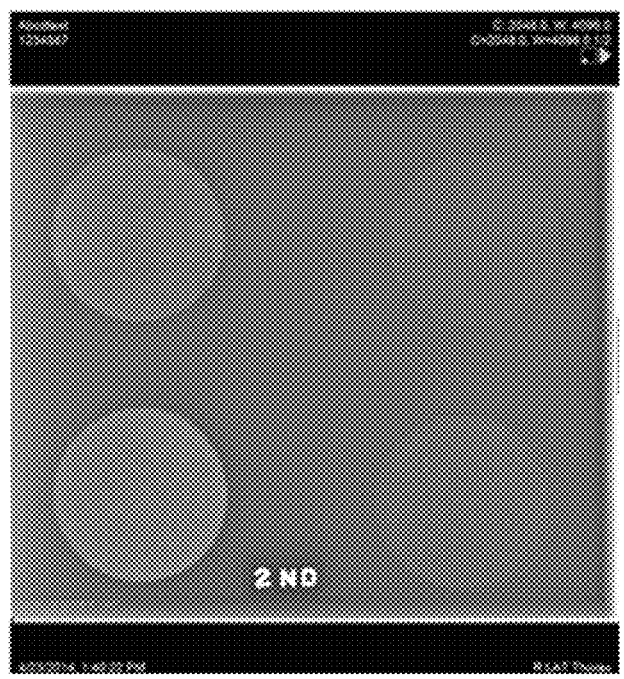
Figure 2G:
Figure 2H:
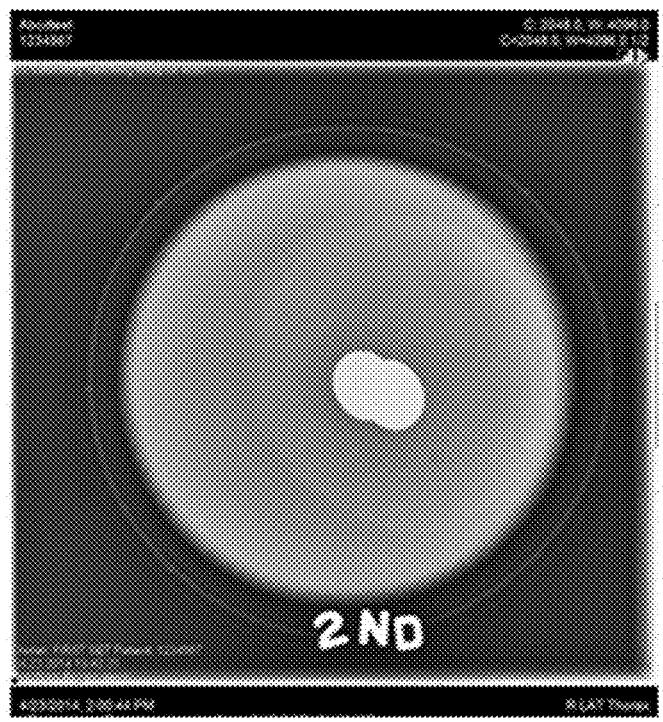

Spun fiber PP with $BaSO_4$. The fiber is spun into pads as shown in FIGS. 2A-2H. The resulting fibers are detectable with X-rays when layers of spun fiber pads are overlayed and imaged by transmitted X-rays. Photograph of extruded polypropylene fiber containing 30.0 wt % barium sulfate particles (FIG. 2A), X-ray film of extruded polypropylene fiber containing 30.0 wt % barium sulfate particles (FIG. 2B), photograph of pad cut from melt-blown polypropylene fiber containing 30.0 wt % barium sulfate particles (FIG. 2C), X-ray film of pad cut from melt-blown polypropylene fiber containing 30.0 wt % barium sulfate particles (FIG. 2D), X-ray transmission images of barium sulfate/propylene melt-blown pads clockwise from the first quadrant for 3, 6, 20, and 10 layers that are produced with higher die temperature to yield a comparatively denser pad, as compared to those of FIG. 2F (FIG. 2E), X-ray transmission images of barium sulfate/propylene melt-blown pads clockwise from the first quadrant for 3, 6, 20, and 10 layers that are produced with lower die temperature to yield a fluffier pad (FIG. 2F), X-ray transmission image of barium sulfate/propylene melt-blown as a 10 layer pad submerged in 3.5 inches of water to simulate tissue with a US quarter used as a weight to keep the pad submerged (FIG. 2G), and X-ray transmission image of barium sulfate/propylene melt-blown as a 20 layer pad submerged in 3.5 inches of water to simulate tissue with two US quarters used as a weight to keep the pad submerged (FIG. 2H).

Example 3

Spun fiber PP with $BaSO_4$ and gold nanocrystals. The process of Example 2 is repeated with cooled fibers drawn through a suspension of 3 nm gold nanocrystals prior to take up on a godet roller to obtain a 0.1 total weight percent gold nanocrystal coating fiber that is formed into a pad per Example 2. The resulting pad covalently bonds thiols from a test solution.

Example 4

Spun fiber PP with $BaSO_4$ and anti-mouse IgG-gold nanocrystals. The process of Example 3 is repeated with cooled fibers drawn through a suspension of commercially available 9-11 nm gold nanocrystals bonded to anti-mouse IgG prior to take up on a godet roller to obtain a 0.05 total weight percent gold nanocrystal coating fiber that is formed into a pad per Example 2. The resulting pad covalently bonds mouse IgG from a test solution, based on secondary labelling of the IgG.

Example 5

Spun fiber PP with $BaSO_4$ and gold nanocrystals. The pad of Example 3 is compressed in a test tube and exposed to a buffer solution of 0.3 M NaCl and 10 mM phosphate buffer containing dithiothreitol or mercaptoethanol, (0.1 ml, 100 mM) at 40° C. for 30 minutes to fix the shape of the pad to that of the test tube, after removal therefrom.

Example 6

Spherical aluminum particulate having a Poisson size distribution and an average particle size of 12 microns is mixed into polypropylene (PP) to form pellets with a particulate loading of 20 percent. The particles are melt-spun by running through a five layer screen pack of mesh sized from 30 to 325. Some of the particulate is noted to be flattened or misshaped.

The foregoing description is illustrative of particular embodiments of the invention, but is not meant to be a limitation upon the practice thereof. The following claims, including all equivalents thereof, are intended to define the scope of the invention.

The invention claimed is:

1. A fiber article for use in a food production, a medical production, or a pharmaceutical production environment, said article comprising:
    a melt-spun polymer fiber having a cross-section and a length; and
    a detectable non-ferrous particulate distributed in the melt-spun polymer fiber, the detectable non-ferrous particulate having present in an amount of 20 to 80 weight percent loadings of metal to render the polymer fiber detectable, alone or in combination with a secondary functional particulate distributed in or on the polymer fiber to render the polymer fiber chemically responsive to a chemical reactant, change in pH or temperature;
    wherein said detectable non-ferrous particulate comprises a plurality of spherical particles and a plurality of asymmetrically deformed or flattened and misshaped particles formed from spherical particles, said particulate distributed in said polymer;
    wherein said detectable non-ferrous particulate is detectable by X-ray detection or magnetic detection with the proviso that when said non-ferrous particulate contains nickel or cobalt, said non-ferrous particulate is nickel alloys or cobalt alloys; and
    wherein said melt-spun polymer fiber combined with said detectable non-ferrous particulate and said secondary functional particulate, when present has a weight per unit length of at least 2.0 denier.

2. The article of claim 1 wherein the detectable non-ferrous particulate has a shortest linear dimension, as measured from among the three orthogonal Cartesian coordinate axes X-Y-Z that is less than or equal to one half the melt-spun polymer fiber cross-sectional average dimension along the three orthogonal Cartesian coordinate axes X-Y-Z.

3. The article of claim 1 wherein the detectable non-ferrous particulate is one of bronze, brass, aluminum, magnesium, boron, barium salts, cobalt, titanium, tin, copper, tungsten, platinum, silver, bismuth, zinc, lead, molybdenum, neodymium, samarium, alloys of any of the aforementioned, oxides of any of the aforementioned metals, or nitrides of any of the aforementioned.

4. The article of claim 1 wherein the detectable non-ferrous particulate are flattened spheroids.

5. The article of claim 1 wherein the polymer fiber is one of polypropylene, polyethylene, polybutene, polyisobutylene, a polyamide, a polyacrylate, a polystyrene, a polyurethane, an acetal resins, a polyethylene vinyl alcohol; a polyester, a polyphenylene sulfide, a thermoplastic elastomers, a polyacrylonitrile; a cellulose, a polyaramid, or a block copolymer containing at least one of the aforementioned.

6. The article of claim 1 wherein the polymer fiber is a single composition with the cross section that is one of circular, multi-lobal or polygonal.

7. The article of claim 1 further comprising a sheath surrounding the polymer fiber.

8. The article of claim 7 further comprising a particulate loaded dusting intermediate between said polymer fiber and said sheath.

9. The article of claim 1 wherein said polymer fiber has a diameter between 0.1 and 500 microns.

10. The article of claim 1 wherein the secondary functional particulate comprises a metallic nanocrystal.

11. The article of claim 1 wherein the secondary functional particulate is present from 0.01 to 5 total weight percent.

12. The article of claim 1 wherein the secondary functional particulate comprises a gold nanocrystal.

13. The article of claim 12 further comprising a moiety covalently bonded to the gold nanocrystal.

14. The article of claim 1 wherein the article defines a shape of a hair net, a protective suit, a shoe cover, a wipe, a scrub pad, packaging, an apron, a beard cover, or a mop head.

15. A process of detecting a fabric article comprising:
forming a polymer fiber having a cross-section and a length and a detectable non-ferrous particulate distributed in the polymer fiber according to claim 1;
forming a fabric at least partly from said fiber;
manufacturing the fabric article at least partly from said fabric;
passing the fabric article through an X-ray detector or a magnetic detector; and
collecting a signal from said X-ray detector or said magnetic detector indicative of the presence of the fabric article.

16. The process of detecting the fabric article of claim 14 wherein the fabric article is a medical device.

17. The process of detecting the fabric article of claim 14 wherein the fabric article is non-woven.

* * * * *